United States Patent [19]

Campbell et al.

[11] Patent Number: 5,074,318
[45] Date of Patent: Dec. 24, 1991

[54] ANIMAL MARKER

[75] Inventors: Neil E. Campbell, Hasbrouch Heights; Chinsoo Park, Rutherford, both of N.J.

[73] Assignee: Bio Medic Data Systems, Inc., Maywood, N.J.

[21] Appl. No.: 444,901

[22] Filed: Dec. 4, 1989

Related U.S. Application Data

[60] Division of Ser. No. 248,451, Sep. 23, 1988, Pat. No. 5,002,548, which is a continuation-in-part of Ser. No. 919,152, Oct. 6, 1986, Pat. No. 4,787,384.

[51] Int. Cl.$^5$ ............................................. A01K 11/00
[52] U.S. Cl. .................................... 128/899; 128/631; 40/300
[58] Field of Search ...................... 119/51.02; 128/899, 128/903, 420.6, 631; 455/100; 604/891.1; 600/7, 8, 12; 40/300

[56] References Cited

U.S. PATENT DOCUMENTS

| | | | |
|---|---|---|---|
| 2,154,205 | 4/1939 | Irwin | 312/67 |
| 2,907,327 | 10/1959 | White | 128/217 |
| 3,016,895 | 11/1962 | Sein | 128/217 |
| 3,144,017 | 8/1964 | Muth . | |
| 3,453,546 | 7/1969 | Fryer . | |
| 3,541,995 | 11/1970 | Fathauer . | |
| 3,572,335 | 3/1971 | Robinson | 128/217 |
| 3,620,216 | 11/1971 | Szymanski | 128/217 |
| 3,820,545 | 6/1974 | Jefferts | 120/330 |
| 4,233,964 | 11/1980 | Jefferts et al. | 128/330 |
| 4,262,632 | 4/1981 | Hanton | 119/1 |
| 4,263,910 | 4/1981 | Pardekooper et al. | 128/217 |
| 4,312,347 | 1/1982 | Magoon et al. | 604/891.1 |
| 4,451,253 | 5/1984 | Harman | 604/60 |
| 4,518,384 | 5/1985 | Tarello et al. | 604/61 |
| 4,672,967 | 6/1987 | Smith | 128/330 |
| 4,679,559 | 7/1987 | Jefferts | 128/330 |

FOREIGN PATENT DOCUMENTS

| | | |
|---|---|---|
| 0042719 | 12/1981 | European Pat. Off. . |
| 0090899 | 10/1983 | European Pat. Off. . |
| 0806702 | 6/1951 | Fed. Rep. of Germany . |
| 2242064 | 3/1975 | France . |
| 60-224428 | 11/1985 | Japan . |
| 60-235188 | 11/1985 | Japan . |
| 61-19438 | 1/1986 | Japan . |
| 61-500040 | 1/1986 | Japan . |
| 61-500241 | 2/1986 | Japan . |
| 61-65286 | 4/1986 | Japan . |
| 61-81741 | 4/1986 | Japan . |
| 61-158728 | 7/1986 | Japan . |
| WO84/01688 | 5/1984 | PCT Int'l Appl. . |
| WO86/00498 | 1/1986 | PCT Int'l Appl. . |
| 472560 | 9/1937 | United Kingdom . |
| 1525841 | 9/1978 | United Kingdom . |
| 2188028 | 9/1987 | United Kingdom . |

OTHER PUBLICATIONS

"A Miniature Transmitter for Telemetering Muscle Potentials", IEEE Transactions on Bio-Medical Electronics, vol. BME-10, No. 3, Jul. 1963, pp. 117-119, Kuck et al.

Primary Examiner—Michael H. Thaler
Attorney, Agent, or Firm—Blum Kaplan

[57] ABSTRACT

A system for implanting a solid marker in an animal is provided. The apparatus includes a hollow tube having an entrance and an exit opening. A support is provided for supporting a hollow tube. A plunger is slideably disposed between a first position and a second position within the support. The plunger cooperates with the support and the tube. The plunger engages the marker proximate to the entrance opening of the tube, and ejects the marker through the tube when the plunger is moved from a first position to a second position. The hollow tubes are stored within the support in at least two groups. A gate prevents a tube from the second group from being displaced before the tubes from the first group as depleted.

2 Claims, 5 Drawing Sheets

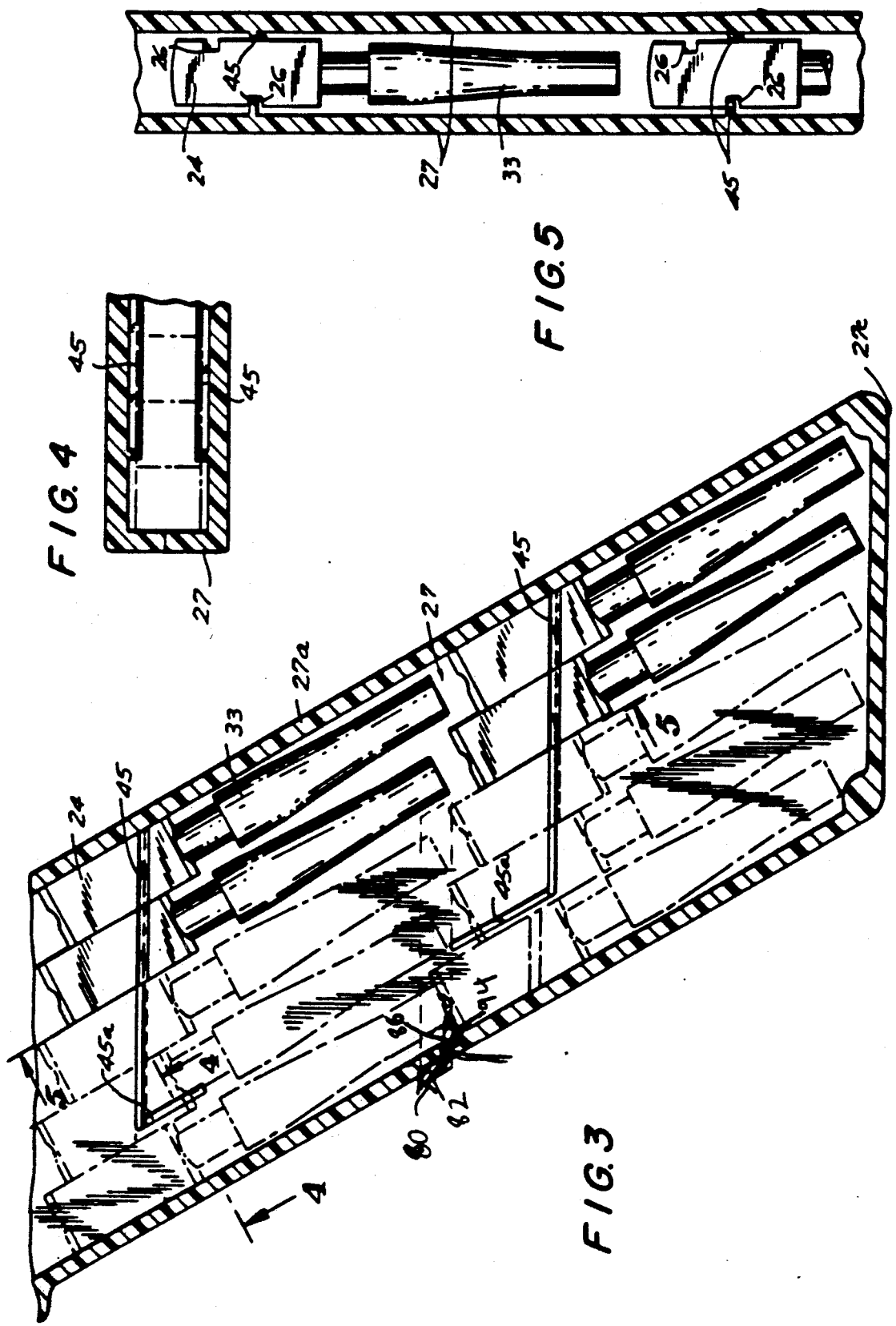

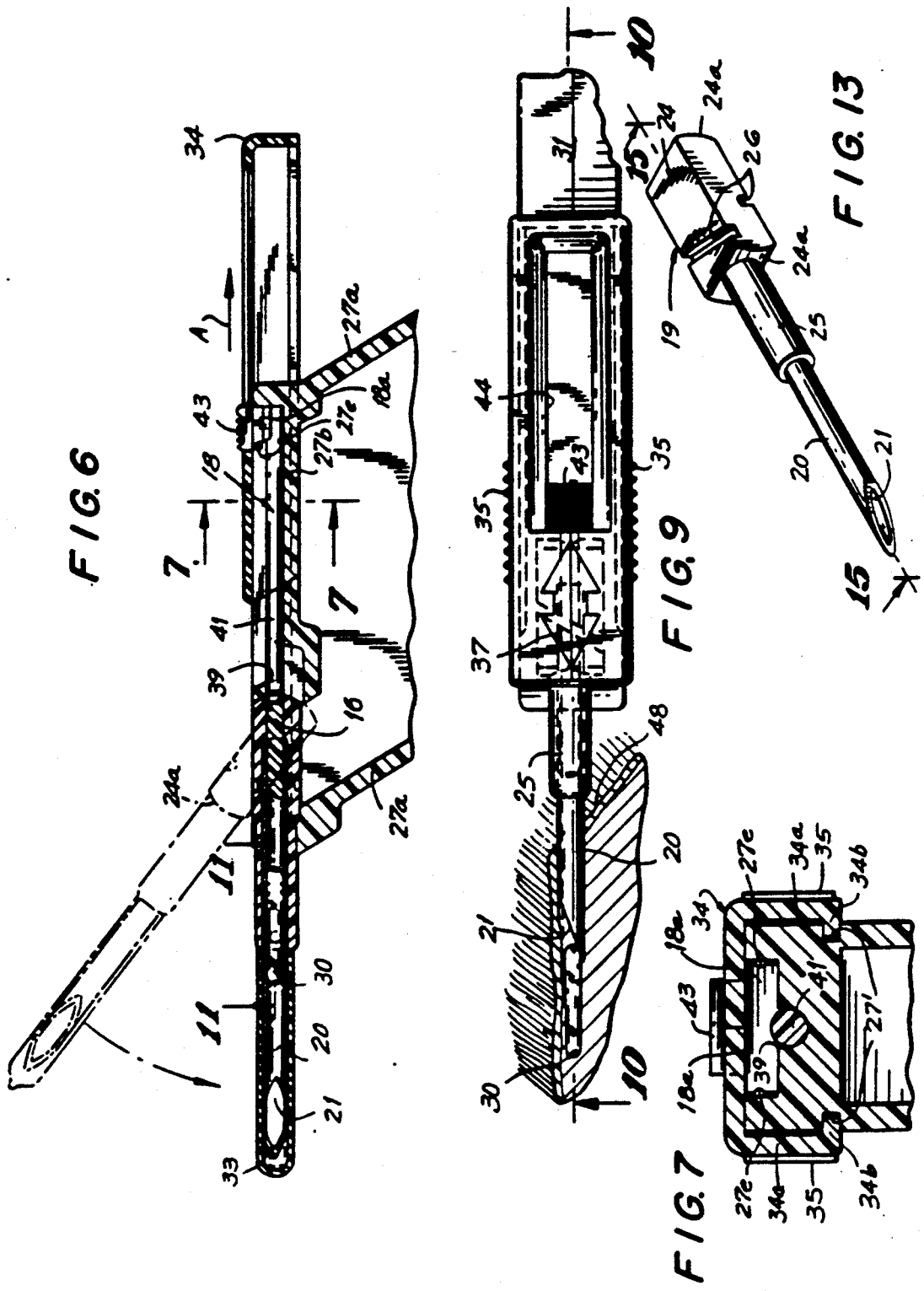

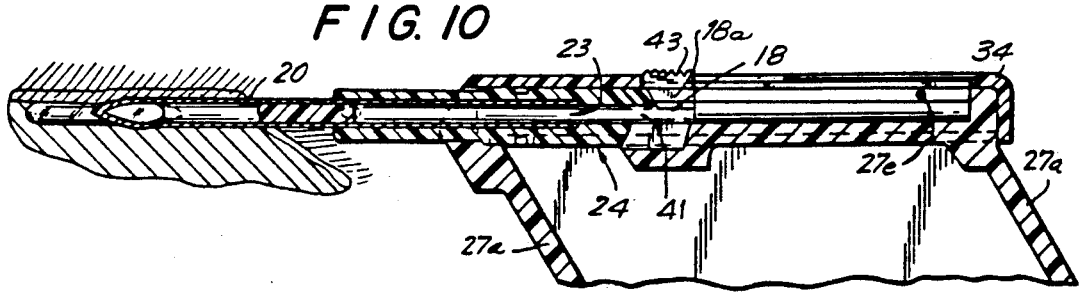
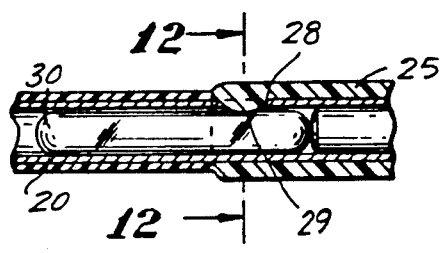
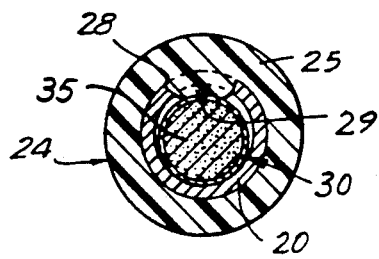
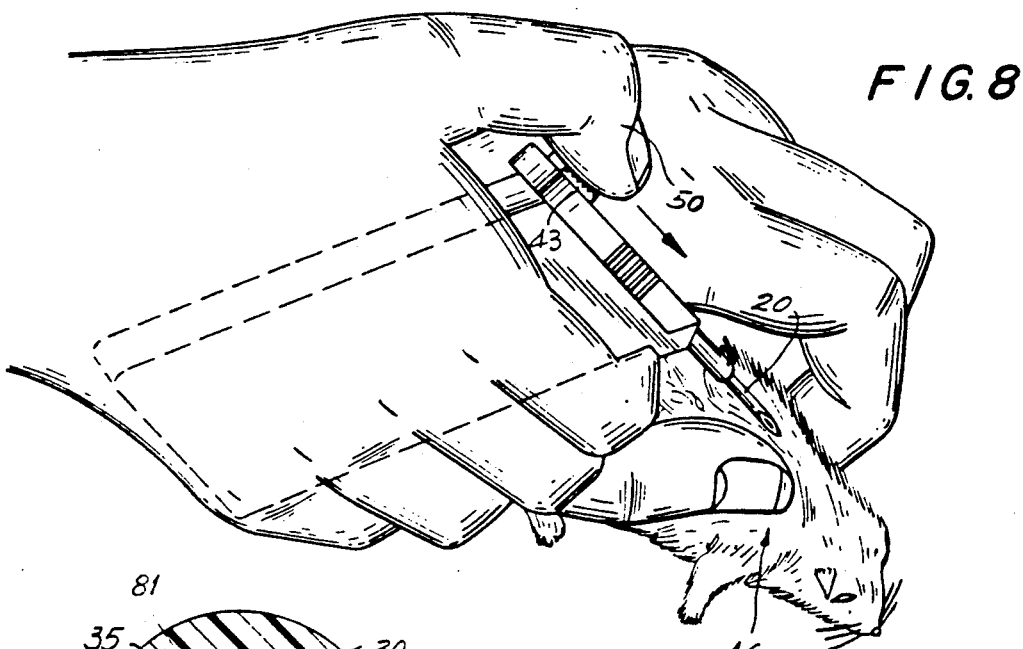
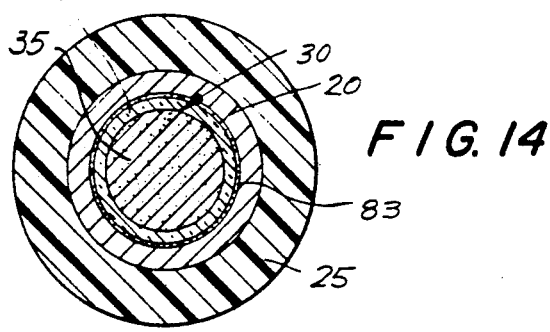

ANIMAL MARKER

CROSS REFERENCE TO RELATED APPLICATION

This is a division of application Ser. No. 07/248,451 filed on Sept. 23, 1988, now U.S. Pat. No. 5,002,548, which is a Continuation-In-Part of U.S. application Ser. No. 06/919,152 filed Oct. 6, 1986 now U.S. Pat. No. 4,787,384.

BACKROUND OF THE INVENTION

This invention relates, in general to a system for implanting an identification marker in an animal and, in particular, to a system for facilitating implantation and retention of an identification marker into a laboratory animal.

Heretofor, the marking of animals for tracking and testing purposes has involved marking the animal externally, i.e. tatooing, branding or tagging. These external markers are difficult to read when identifying the animal and are extremely limited in the amount of information about the animal that can be carried by the external marker.

In order to overcome the disadvantages noted above with external markers, a system has been proposed whereby markers carrying information that can be read by an external detector can be implanted in a test animal. However, such a system requires an instrument that permits a marker to be delivered into the animal without difficulty and wherein the marker will remain securely embedded in the lab animal for a considerable length of time.

SUMMARY OF THE INVENTION

Generally speaking, in accordance with the invention, an improved apparatus for implanting a marker into an animal is provided. The apparatus includes a hollow tube having an opening at each end. An entrance end of the hollow tube is supported within a housing. An exit end of the tube is sharp to allow subcutaneous penetration of the tube underneath the skin of a laboratory animal. A plunger is slideably mounted within the housing. The plunger is adapted to displace the marker from a first position in the tube out of the exit end of the tube. The tubes are stored within the instrument itself in a series of rows. A gate clip prevents each successive row of tubes from intermixing with the previous row of tubes.

In an exemplary embodiment, an electronic transponder containing information about the animal, such as identification numbers, is placed in the marker. When the tube is inserted below the skin of the animal and the plunger is displaced, the marker containing the electronic transponder is forced through the tube, lodging it underneath the skin of the animal.

An object of this invention is to provide an improved apparatus for implanting markers in laboratory animals.

A further object of this invention is to provide an implanting system for facilitating identification of laboratory animals.

Still a further object of this invention is to provide an easy to use implanting instrument for implanting a marker into a laboratory animal.

Yet a further object of the invention is to provide an implanting system for implanting a marker subcutaneously in the animal so that the marker will be retained within the animal.

Yet a further object of the invention is to provide an implanting system for implanting a marker subcutaneously in the animal so that the marker will be retained within the animal.

The invention accordingly comprises features of construction, combination of elements and arrangement of parts which will be exemplified in the construction hereinaftert set forth and the scope of the invention will be indicated in the claims.

BRIEF DESCRIPTION OF THE DRAWINGS

For a fuller understanding of the invention, reference is had to the following description taken in connection with the accompanying drawings, in which:

FIG. 3 is a partial sectional view taken along line 2—2 of FIG. 1;

FIG. 4 is a partial sectional view taken along line 4—4 of FIG. 3;

FIG. 5 is a partial sectional view taken along line 5—5 of FIG. 3;

FIG. 6 is a partial sectional view taken along line 2—2 of FIG. 1, when the needle assembly is inserted therein;

FIG. 7 is a sectional view taken along line 7—7 of FIG. 6;

FIG. 8 is a perspective view of the implanting instrument illustrated in FIG. 1 in use;

FIG. 9 is a plan view of the implanting instrument illustrated in FIG. 1 in use;

FIG. 10 is a sectional view taken along line 10—10 of FIG 9;

FIG. 11 is an enlarged partial sectional view of the implanter instrument illustrated in FIG. 10;

FIG. 12 is a sectional view of the implanting instrument taken along line 12—12 of FIG. 11;

FIG. 13 is a perspective view of the needle assembly;

FIG. 14 is a sectional view of the marker depicted in FIG. 11;

DETAILED DESCRIPTION OF THE PREFERRED EMBODIMENTS

Figure 1:
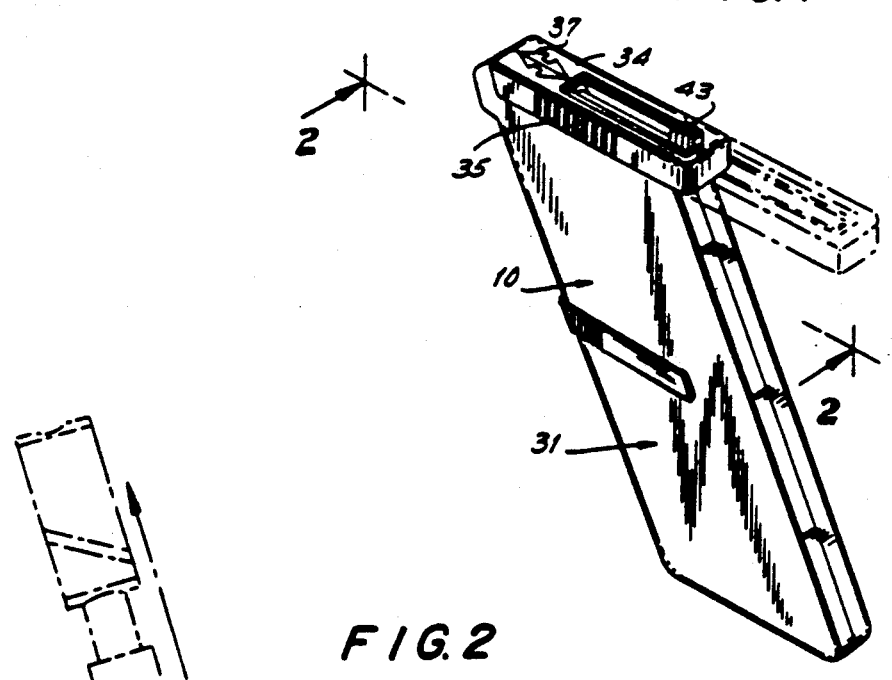
FIG. 1 is a perspective view of an animal marker implanting instrument constructed in accordance with a preferred embodiment of the instant invention.

Reference is initially made to FIGS. 1 through 15, wherein an animal marking system including an implanting instrument, generally indicated at 10 (FIG. 1), a needle assembly, generally indicated as 19 (FIG. 13) and an animal marker, generally indicated as 30 (FIGS. 11, 12 and 14) is depicted. As is explained in greater detail below, the cooperation of the needle assembly, marker and implanting instrument permits the facile implantation of a marker into a laboratory animal and the retention of the marker within the animal during long periods of laboratory monitoring and testing.

Reference is now particularly made to FIGS. 1 through 5, wherein instrument 10 is illustrated in detail. Instrument 10 defines two opposed half walls 27 which are molded in mirror image and secured together to define a unitary housing in the shape of a handle 31. Each opposed wall 27 is defined by a substantially parallelogram shaped configuration including lengthwise mating walls 27a and lateral mating walls 27b and 27c. As is explained in greater detail below, mating walls 27a are inclined with respect to lateral mating walls 27b to define handle 31 and to facilitate storage therein of a plurality of needle assemblies. A cap 34 is slideably mounted to the housing defined in opposed wall 27. In an exemplary embodiment, at least one of the opposed walls 27 can be transparent or translucent to allow the user to view the needle assemblies 19 disposed within the handle.

Figure 2:
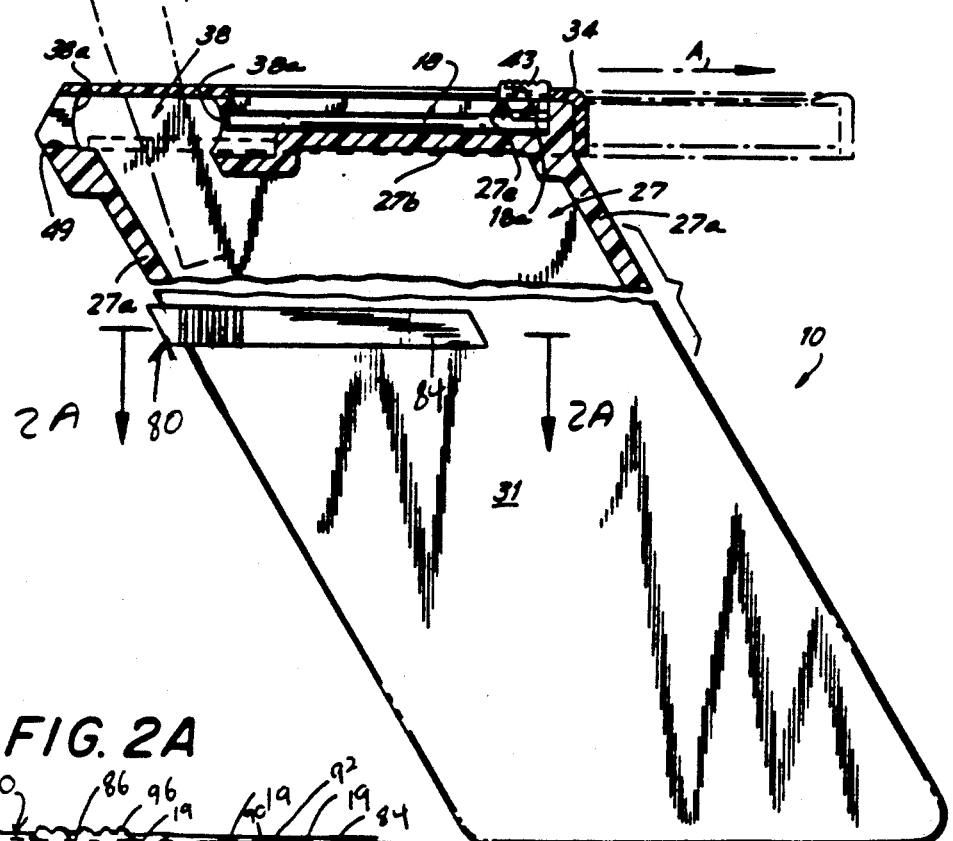
FIG. 2 is a partial sectional view taken along line 2—2 of FIG. 1.
Figure 2A:
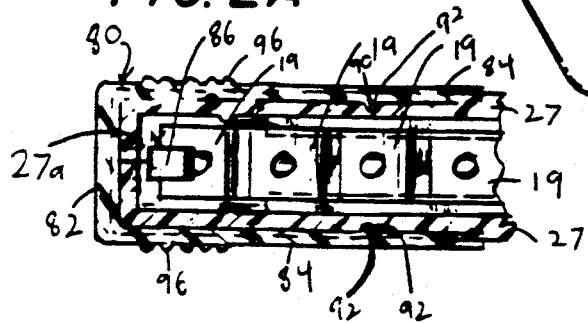
FIG. 2A is a sectional view taken along lines 2A—2A of FIG. 2.
Figure 15:
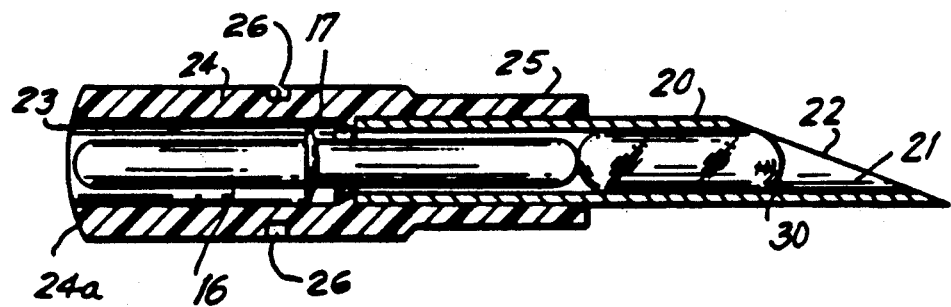
FIG. 15 is a sectional view taken along line 15—15 of FIG. 13.

Cap 34 is normally disposed in a closed position, and can be displaced in the direction A (FIG. 2) from a closed position (solid lines in FIG. 2) to an open position (phantom lines in FIG. 2). As is illustrated in FIG. 7, cap 34 includes side walls 34a and gripping walls 34b which are disposed in elongated slots 27' formed in opposed walls 27. Cap 34 includes ribs 35 on the side for permitting the cap to be easily gripped and can be displaced between an open and closed position. An arrow 37 or other indicia can be imprinted on cap 34 to indicate the proper directions for sliding.

Opposed lateral walls 27b are covered by cap 34 when cap 34 is in a closed position. Opposed lateral walls 27b are configured to define opposed recessed walls 38a and an open chamber, generally indicated at 38, for receiving a needle assembly and for permitting each needle assembly to be dispensed through the opening from the interior of the housing when cap 34 is displaced to an open position. Opposed lateral walls 27b are further configured to define a channel 39 which orients the needle assembly when it is positioned in chamber 38.

Referring particularly to FIGS. 10 through 15, needle assembly 19 is formed from a stainless steel hollow tube 20 having an exit opening 21 and an entrance opening 23. Exit opening 21 is formed in the shape of an inclined edge 22 which forms a sharp point for permitting the tube to easily penetrate an animal's skin. The side of tube 20 having entrance opening 23 is molded in a plug 24. Plug 24 includes a sleeve 25 integrally formed therewith and projecting about tube 20 to extend along a portion of the tube's length. Plug 24 includes arcuate end walls 24a for facilitating the positioning of the plugs in chamber 38 in a manner that will be discussed in detail below. As is particularly illustrated in FIG. 15, marker 30 is positioned in tube 20 near the exit opening 21 thereof. A drive pin 16 is used to position the marker within the tube. Drive pin 16 includes a sealing disc 17 that is integrally molded therewith. Sealing disc 17 has an outside diameter that is sufficient to interference fit with the inside diameter of the tube 20 and prevent displacement of the drive pin during normal storage and handling of the needle assembly. Drive pin 16 aids in positioning the marker in the tube. However, it has been found necessary to facilitate positioning of the marker in tube 20 particularly when the marker is a glass capsule in order to prevent the marker from slipping out of the exit opening of the tube.

Reference is now made to FIGS. 11 and 12 wherein a projection 29 integral with sleeve 25 extends through opening 28 in order to prevent the marker from slipping or moving in the tube prior to the discharge of same into the animal. This projection can be easily formed during assembly of the hollow tube within plug 24 by molding the plug about the tube and permitting the resin used to form the tube to enter aperture 28. Projection 29 is intended to frictionally engage marker 30 when the marker is positioned within tube 20 to prevent the marker from sliding in the tube. Projection 29 will hold the marker in place until a force sufficient to push marker 30 through tube 20 is applied to a plunger and, in turn, to the marker.

In an exemplary embodiment, tube 20 is stainless steel. However, tube 20 may be made from other rigid FDA approved materials, such as Ultem ®, manufactured by General Electric. Also, as aforenoted, sleeve 25 and plug 24 can be integrally formed by injection molding a plastic resin about the entrance opening of tube 20. Also, the sleeve and plug may be formed of rigid materials other than plastic.

Needle assembly 19 is easily positioned in chamber 38 when cap 34 is displaced into an open position. Moreover, needle assembly 19 is tightly secured within chamber 38 by returning cap 34 to a closed position. This prevents any wobbling of the needle assembly 19 during use.

Plunger 18 includes a rod 41 and a knurled surface 43 integrally formed at one end of rod 41. Plunger 18 is slideably mounted within elongated channel 39 formed by lateral walls 27b formed in the top of the housing. Knurled surface 43 projects through elongated opening 44 in cap 34 and permits the plunger to be displaced between a start position and an implanting position. Channel 39 is coaxially aligned with the entrance opening 23 of tube 20 of the needle assembly 19 and alignment channel 49 to form a continuous pathway for rod 41 when needle assembly 19 is retained in chamber 38. Knurled surface 43 extends through elongated opening 44 (FIG. 9) in cap 34, allowing displacement of the plunger 18 by pushing knurled surface 43 from a start position to an implanting position. Plunger 18 also includes seats 18a projecting therefrom which rests against stops 27e formed by opposed half walls 27. Stops 27e and seats 18a cooperate to normally maintain the plunger at the start position depicted in FIG. 6.

The distance of the placement of the marker in the tube from the exit opening and the length of elongated opening 44 have relative lengths with respect to each other. When cap 34 is displaced in the direction A into an open position, it will capture knurled surface 43 if it is not already in a start position and displace the plunger to a start position so that rod 41 is entirely displaced outside of the entrance opening 23 of the needle assembly 19. Furthermore, the distance of the placement of the marker from the exit opening determines the distance through which the rod will be displaced and, hence, the preferred distance of elongaged opening 44. Moreover, this distance further assumes that rod 41 is entirely displaced without the entrance opening of the tube when plunger 18 is in a start position. This permits placement of needle assembly 19 in chamber 38.

When cap 34 is returned to a closed position, stop 27e helps maintain plunger 18 at its start position so that the plunger is not unintentionally pushed forward. If slideable cap 34 is not pushed entirely into a closed position, knurled surface 43 is prevented from being pushed forward sufficiently to cause plunger 18 to eject the marker 28 from the needle assembly 19. This configuration prevents use of the instrument unless the needle assembly 19 is fully secured within chamber 38 and is securely captured by cap 34 being displaced into a closed position. Also, since knurled surface 43 of the plunger 18 comes in contact with the cap at the limits of elongated opening 44, the plunger 18 is automatically positioned by manipulating the cap.

Reference is now also made to FIG. 8, wherein operation of the instant invention is depicted. In an exemplary embodiment, marker 30 is stored within tube 20 and is retained therein by a projection 25. Cap 34 is then slid into an open position. Needle assembly 19 is then pivotably displaced into chamber 38. Cap 34 is then displaced forward into a closed position supporting and anchoring needle assembly 19 securely in place within chamber 38 and channel 49.

Figure 16:
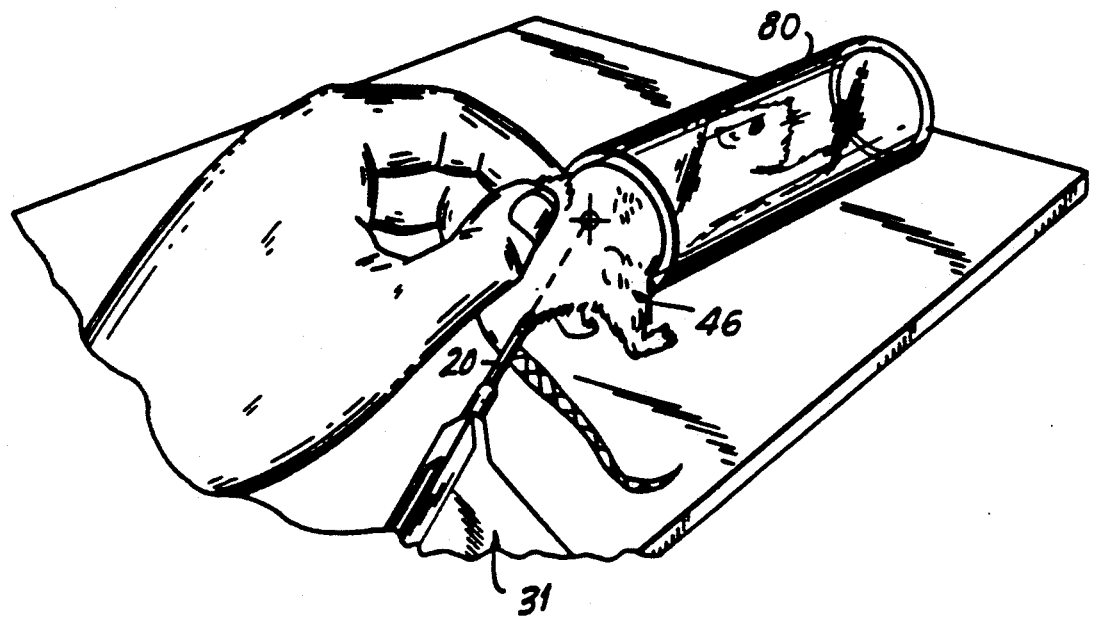
FIG. 16 is a perspective view of a cylinder to be used as part of the instant invention.

Next, a test animal, such as a mouse 46, must be stabilized. As illustrated in FIG. 8, a mouse can be picked up in the user's one hand and the implanting instrument held in the user's other hand. However, as is illustrated in FIG. 16, in an exemplary embodiment, a cylinder 80 that is open at both ends can be utilized to render the head of the mouse immobile. By inserting the mouse's head in a cylinder the mouse cannot turn its head and bite the user's hand or otherwise interfere with the procedure. Furthermore, once the mouse's head is immobilized in the cylinder it permits the hand of the user to be used to stretch the animal's skin and thereby facilitate manipulation of the mouse during subcutaneous implantation. Accordingly, the implanter systems of the instant invention contemplates the use of different sized tubes to accommodate the distinct differences in the size of the laboratory animals. Once the animal is immobilized, the user is prepared to insert tube 20 into the laboratory animal.

Exit end 21 of tube 20 is inserted subcutaneously into mouse 46 until the animal's skin 48 reaches the edge of sleeve 25. This automatically places marker 30 at the desired position beneath the skin. Knurled surface 43 of the plunger 18 is then pushed forward, preferably with the user's thumb 50, with enough force such that plunger 18 engages drive pin 16. Knurled surface 43 is displaced until knurled surface 43 is disposed into an implanting position so that rod 43 comes in contact with the end of opening 44 in cap 34. At this point, plunger rod 41 of plunger 18 has engaged drive pin 16 and extends far enough within tube 20 to have forced drive pin 16 to eject marker 30 from tube 20 underneath the animal's skin. Next, the implanting apparatus is removed from animal skin 48, cap 34 is pulled back and needle assembly 19 is removed and discarded. The process may then be repeated for another animal.

In an exemplary embodiment, marker 30 is a glass capsule having therein an electronic transponder 35 containing identification information about the animal. This is used by way of example only. This process is adaptable to the implantation of any type of marker. Marker 30 is formed by embedding an electronic transponder 35 in a glass capsule. By using an electronic transponder, the amount of storable information is greatly increased, especially when transponder information can be directly linked to computer systems containing further information and processing software. Because the capsule is glass, it tends to slide easily in stainless tube 20. It is for this reason that projection 29 is used to interference fit the capsule in the tube and prevent same from moving within the tube during storage and handling of the needle assembly.

Each needle assembly 19 is sealed within a sanitary sleeve 33 which can be easily removed when the needle assembly is displaced into chamber 38 for use in the manner described above. Moreover, after sanitary sleeve 33 is used to cover the exit opening of the tube, a sterilant gas can be injected into a chamber defined by tube 20, drive pin 16 and sealing disc 17 and the sleeve 33. By introducing a sterilant gas, the marker can be sterilized and remain sterilized until the needle assembly is ready for use. Furthermore, as is illustrated particularly in FIGS. 2 through 5 and 13, the opposed side walls 27 of the housing and the plug 24 of each needle assembly are configured in a manner discussed below to permit each needle assembly to be stored in the handle and removed therefrom for easy use.

Specifically, a pair of opposed ramps 45 are formed in each wall 27. Ramps 45 are formed in mirror image on each wall so that they are disposed in registry with each other when walls 27 are brought together to form the housing defining handle 31. Furthermore, each ramp is disposed in parallel with lateral wall 37c and at an angle with respect to the lengthwise extent of the handle. Ramps 45 are spread a sufficient distance apart to permit two rows of needle assemblies to be stored in handle 31.

The plug of each needle assembly 19 includes positioning grooves 26 found in opposed surfaces, the grooves being disposed on an angle with respect to the lengthwise extent of the plug and diagonally opposed with each other to facilitate placement of each needle assembly 19 in the housing during assembly of the product. As is illustrated with some particularity in FIGS. 3 through 5, each needle assembly can be positioned within handle by racking the plug onto a first ramp 45 so that the ramp is positioned within the positioning groove 26. The groove 26 and ramp 45 prevent any substantial lengthwise displacement of each needle assembly during storage and use of the instrument. The opposing ramp assists in positioning the plug by pressing against the plug. Each ramp 45 includes a positioning ramp 45a that is parallel with the lengthwise side walls 27a of handle 31. Positioning ramp 45a does not protrude as far as ramp 45 and is provided to assist in preventing the plug from sliding laterally and to further assist in guiding the needle assembly through the opening in chamber 38 when a needle assembly is to be removed from the handle.

In an exemplary embodiment, ten needle assemblies are stored on each ramp 45. As noted above, wall 27a and ramp 45a facilitate delivery of each needle assembly to the operator.

As is illustrated in FIG. 2, the opening in chamber 38 is sufficiently large to permit the needle assembly to be removed therethrough. Accordingly, when a needle assembly is needed, cap 34 is displaced from a closed position to an open position. By manipulating the orientation of the housing, a needle assembly positioned closest to chamber 38 will then slide out of the housing through opening 38. As aforenoted, such manipulation can be facilitated by forming one of the opposed walls 27 forming handle 31 out of a transparent or translucent material. It is then a simple matter to position plug 24 of the needle assembly in chamber 38, slide cap 34 to a closed position and remove the sanitary sleeve 33, so that the user is ready to begin implantation of the marker in the manner discussed above.

Reference is now made to FIG. 14, wherein a marker 30 is formed of a smooth material 81, such as glass. As aforenoted, the use of a glass marker can be problematical. First, when the needle assembly does not include a projection 29, marker 30 is not secured in the tube and, hence, the marker may slide out of the tube of the needle assemlby. Also, it has been observed that when a glass encapsulated transponder 35 is implanted in a laboratory animal, migration of the transponder out of the wound of the animal can occur. Accordingly, in a preferred embodiment, one-half of marker 30 is coated with a layer 83 having a high coefficient of friction. For example, Silastic ®, manufactured by Dow Corning, has been successfully used. Also, polypropylene has been used as a coating. By utilizing a layer coating marker 30, projection 29 can be eliminated, thereby allowing for a thinner tube 20 having a greater inner diameter than the embodiments containing projection 29.

The instant invention further contemplates a method of forming layer 83 about a glass marker. Specifically, markers are partially inserted into a mold cavity. Thereaftrer, a polypropylene resin is injected into the mold cavities and cured about the marker to define a suitable non-slippery surface.

In a further embodiment, the outer surface of glass of marker 30 can be etched. Although etching of the outer glass coating prevents migration in the animal, projection 29 is still needed to hold marker 30 in place in the tube 20. However, etching has been found to weaken the marker and although experimentally viable, does not appear to offer the same efficiency as the use of a coating on the glass capsule.

It will thus be seen that the objects set forth above, and those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cap all of the generic and specific features of the invention herein described, and all statements of the scope of the invention which, as a matter of language, might be said to fall therebetween.

What is claimed is:

1. A marker adapted to be injected subcutaneously into a laboratory animal by an implanting apparatus comprising a glass capsule having therein an electronic transponder, and anti-migration means covering at least a portion of said capsule, said anti-migration means preventing migration of the marker from said laboratory animal.

2. A marker as claimed in claim 1, wherein said anti-migration means includes a layer coating at least a portion of the surface of the capsule.

* * * * *